United States Patent [19]

Hartman et al.

[11] Patent Number: 5,180,802
[45] Date of Patent: Jan. 19, 1993

[54] MONOAMINE CAPPED NON-REACTIVE POLYAMIDE COMPOSITION

[75] Inventors: Terrence L. Hartman, New Brunswick; Charles A. Cody, Robbinsville, both of N.J.

[73] Assignee: Rheox, Inc., Hightstown, N.J.

[21] Appl. No.: 553,581

[22] Filed: Jul. 18, 1990

[51] Int. Cl.$^5$ .............................................. C08G 69/00
[52] U.S. Cl. ................................... 528/335; 528/332; 528/336; 528/339.3; 564/152; 564/153; 564/155; 564/157; 564/159
[58] Field of Search ............ 528/335, 332, 336, 339.3; 260/404.5 PA; 564/152, 153, 155, 157, 159

[56] References Cited

U.S. PATENT DOCUMENTS

| | | | |
|---|---|---|---|
| 2,130,948 | 9/1938 | Carothers | 528/335 |
| 2,153,801 | 4/1939 | Hovey et al. | 528/332 |
| 2,230,326 | 2/1941 | Hovey et al. | 528/335 |
| 3,412,115 | 11/1968 | Floyd et al. | |
| 3,957,733 | 5/1976 | Rogier et al. | |
| 4,055,525 | 10/1977 | Cheng | |
| 4,722,963 | 2/1988 | Whyzmuzis | 528/335 |
| 4,778,843 | 10/1988 | Cooperman et al. | 528/335 |
| 4,816,551 | 3/1989 | Oehler et al. | 528/335 |

FOREIGN PATENT DOCUMENTS

| 210157 | 1/1987 | European Pat. Off. |
|---|---|---|
| 2177411A | 1/1987 | United Kingdom |
| 2177412A | 1/1987 | United Kingdom |

OTHER PUBLICATIONS

Hackh's Chemical Dictionary, Fourth Edition, 1980, p. 533.

Primary Examiner—Harold D. Anderson
Attorney, Agent, or Firm—Burns, Doane, Swecker & Mathis

[57] ABSTRACT

The invention relates to alkyl- or aryl-terminated polyamide compositions and polyamide rheological additives that function as a sag/slump control agent and provide superior shear-thinning and viscosity recovery properties in systems that react with or are sensitive to water and other active hydrogen containing materials and systems that do not react with or are not sensitive to water or other active hydrogen containing materials, and are useful in sealants, caulks, adhesives and coatings.

11 Claims, No Drawings

MONOAMINE CAPPED NON-REACTIVE POLYAMIDE COMPOSITION

FIELD OF THE INVENTION

The present invention relates to alkyl- and aryl-terminated polyamide compositions that function as rheological additives including sag/slump control agents when incorporated into sealant, caulk, adhesive and coating formulations, and provide superior shear-thinning and viscosity recovery properties.

BACKGROUND OF THE INVENTION

Rheological additives have been widely employed in the formulation of products such as sealants, adhesives and coatings to provide control of sag or slump during and after application. Various organic and inorganic materials such as fumed silicas, carbon blacks, asbestos, castor oil derivatives, organo-modified clays, and other minerals, fibers and organic synthetics such as polyurethanes and polyamides, have provided thixotropic properties to end products, particularly non-reactive products.

As set forth in U.S. Pat. No. 4,778,843 granted on Oct. 18, 1988, polyamide rheological additives wherein the polyamide chain is capped with a monocarboxylic acid containing from 16 to 22 carbon atoms and either an olefinic unsaturation or a hydroxyl group have been found to be effective in thickening non-reactive organic solvent based coating systems.

U.S. Pat. No. 4,670,173 granted on Jun. 2, 1987 discloses oil-soluble compositions that are useful as viscosity modifiers. Such compositions are formed by reacting an acylating product, a polyamine and a mono-functional acid either in the presence of a hydrocarbon solvent or in the absence of a solvent.

U.S. Pat. No. 4,462,926 granted on Jul. 31, 1984 discloses a polyamide thixotrope for unsaturated polyester resins consisting of at least one cyclohexyl amide of a saturated fatty acid which contains at least 10 carbon atoms and at least one oligomeric ester amide having an average molecular weight of from 600 to 3000, a content of carboxylic acid amide groups of from 1.5% to 15% by weight and a content of carboxylate groups of from 2% to 13% by weight.

Copending patent application Ser. No. 336,002, filed Apr. 10, 1989, U.S. Pat. No. 5,075,407 describes polyamides of one type shown in the specification for use as encapsulants during agents melt adhesives.

However, in many systems either the basic components show appreciable reactivity toward such conventional rheological additives or the additives are simply impractical due to inferior performance, cost or the impartation of undesirable side effects. One such system is the one component moisture cured polyurethane sealants. Such sealants are based on urethane prepolymers with reactive isocyanate functionality. The isocyanate groups of these molecules react readily with active hydrogen containing species such as water, primary and secondary amines, hydroxyls, carboxyls and mercaptans. Many of the conventional rheological additives such as fumed silicas, castor oil derivatives and organomodified clays contain one or more types of these active hydrogen groups and therefore cause detrimental effects to the sealant such as interference with cure rate, final physical properties or package stability. Additionally, the additives are often rendered inactive due to the consumption of active hydrogen groups by the isocyanate groups of the urethane prepolymer.

Some existing rheological additives are relatively inert toward isocyanates if dried and employed under anhydrous conditions. However, their use is limited by other factors. For example, the use of asbestos has been essentially eliminated due to its carcinogenicity. Fine particle/high structure carbon blacks are only effective at high concentrations and also render the sealant black in color. Further, various organic fibers are either high in cost, low in efficiency or provide an undesirable appearance to the sealant product.

Still other products or techniques have been employed such as PVC plastisol fusion, but such processes are very process sensitive or labor intensive.

Polyamides of certain types have been shown to impart thixotropy in various resin or solvent systems. However, polyamides typically possess active hydrogen functionality such as amines or carboxylic acids. As set forth in U.S. Pat. No. 4,778,843, recently introduced polyamide rheology modifying agents have hydroxyl functionality. Such active hydrogen containing species react with isocyanates resulting in final product instability, cure impediment, rheology deactivation or other detrimental effects.

A need exists in the art for a rheological additive that overcomes the foregoing shortcomings.

SUMMARY OF THE INVENTION

The present invention overcomes the problems and disadvantages of the prior art by providing alkyl- and aryl-terminated non-reactive polyamide rheological additives that exhibit superior properties over prior art rheological additives when incorporated into sealants, caulks, adhesives and coatings.

It is an object of the present invention to provide polyamide rheological additives that do not contain appreciable levels of active hydrogen containing species.

It is a further object of the invention to provide polyamide rheological additives that can be easily incorporated in and are compatible with sealant, caulk, adhesive and coating formulations.

It is an additional object of the invention to provide polyamide rheological additives that provide shear-thinning characteristics, i.e., high viscosity at low shear rates and low viscosity at high shear rates, to systems in which the polyamide rheological additives are incorporated. A measure of this property is the thixotropic index, T.I., where $$T.I. = \frac{\text{Viscosity @ shear rate 1}}{\text{Viscosity @ shear rate 2}}$$

and shear rate 1 is less than shear rate 2.

It is yet a further object of the invention to provide polyamide rheological additives that exhibit recovery of initial viscosity immediately after application of shear to the end use system.

Additional objects and advantages of the invention will be set forth in part in the description which follows, and in part will be obvious from the description, or may be learned by practice of the invention. The objects and advantages of the invention will be realized and attained by means of the instrumentalities and combinations, particularly pointed out in the appended claims.

To achieve the objects and in accordance with the purpose of the invention, as embodied and broadly described herein, the invention provides alkyl- and aryl-terminated polyamide rheological additives useful in sealant, caulk, adhesive and coating formulations. The polyamide rheological additives are prepared by the following reactions (1)–(4):

Reaction (1): reacting at least one polycarboxylic acid of the formula

(A)[COOH]$_x$  (I)

wherein $x \geq 2$ and A is selected from the group consisting of aliphatic, aromatic, cycloaliphatic and arylaliphatic groups with at least one monoamine of the formula

(G)NH  (II)

wherein G is selected from the group consisting of aliphatic, aromatic, cycloaliphatic and arylaliphatic groups, and wherein the monoamine may include primary amines and/or secondary amines, and when the monoamine contains a primary amine, the additional hydrogen atom is included in the (G) moiety, to form a polyamide of the formula

(G)NOC(A)CON(G)  (a)

Reaction (2): reacting at least one polycarboxylic acid of the formula (I) with
at least one monoamine of the formula (II), and
at least one polyamine of the formula

(D)[NH]$_y$  (III)

wherein $y \simeq 2$ and D is selected from the group consisting of aliphatic, aromatic, cycloaliphatic and arylaliphatic groups, and wherein the polyamine may include primary amines and/or secondary amines, and when the polyamine contains a primary amine, the additional hydrogen atom is included in the (D) moiety, to form a polyamide of the formula (G)NOC(A)CO[N(D)NOC(A)CO]$_n$ N(G)  (b)

wherein $n = 1$ to $\infty$.

Reaction (3): reacting at least one polyamine of the formula (III) with
at least one monocarboxylic acid of the formula

(E)COOH  (IV)

wherein E is selected from the group consisting of aliphatic, aromatic, cycloaliphatic and arylaliphatic groups to form a polyamide of the formula

(E)CON(D)NOC(E)  (c)

Reaction (4): reacting at least one polycarboxylic acid of the formula (I) with
at least one polyamine of the formula (III) and,
at least one monocarboxylic acid of the formula (IV), to form a polyamide of the formula
(E)CON(D)N[OC(A)CON(D)N]$_n$ OC(E)  (d)

wherein $n = 1$ to $\infty$.

The polyamide rheological additives of the invention may also be prepared by reacting to form mixtures of any of the reaction products formed from any of above reactions (1)–(4).

The formulas of polycarboxylic acids and polyamines set forth above only include those with a functionality of two, i.e. $x = 2$, $y = 2$, for illustrative convenience. Polycarboxylic acids and polyamines with a functionality of three or greater may also be employed. Each branch point chain resulting from inclusion of such higher functionality materials will follow a similar pattern of polyamide chain structure as those illustrated above.

The above reactions may or may not be carried out in the presence of a catalyst.

As used herein, the term "polyamide" includes any of the products of the reactions (1)–(4) set forth above wherein the average number of amide linkages is at least about two.

As used herein, the term "polycarboxylic acid" includes all aliphatic or aromatic carboxylic acids having a functionality of at least two, as well as the corresponding acid anhydrides, esters and acid halides.

As used herein, the term "polyamine" includes all aliphatic or aromatic primary or secondary amines having a functionality of at least two.

As used herein, the term "monocarboxylic acid" includes all aliphatic or aromatic carboxylic acids having a functionality of one, as well as the corresponding acid anhydrides, esters and acid halides.

As used herein, the term "monoamine" includes aliphatic or aromatic primary or secondary amines having a functionality of one.

The molar quantities of the reactants of reactions (1) through (4) are whole numbers with the exception that the moles of monocarboxylic acid of the formula (IV), or the monoamine of the formula (II), may be a fractional quantity if the average functionality of the polyamine and/or polyacid containing backbone is fractional, since the moles of capping agent is equal to the functionality of the backbone.

In reaction (1), at least 2.0 moles of monoamine are employed. The moles of monoamine equal the average functionality of the polycarboxylic acid. 1.0 mole of polycarboxylic acid is employed.

In reaction (2), at least 2.0 moles of monoamine are employed. The moles of monoamine equal the average functionality of acid-terminated polyamide from the reaction of the polycarboxylic acid and the polyamine. At least 2.0 moles of polycarboxylic acid are employed, and the moles of polycarboxylic acid employed are the same as or greater than the moles of polyamine employed. The equivalents of polycarboxylic acid are greater than or equal to the equivalents of polyamine plus 2.0. The equivalents of polycarboxylic acid minus the equivalents of polyamine equal the equivalents of monoamine.

In reaction (3), at least 2.0 moles of monocarboxylic acid are employed. The moles of monocarboxylic acid are equal to the average functionality of the polyamine. 1.0 moles of polyamine is employed.

In reaction (4), at least 2.0 moles of monocarboxylic acid are employed. The moles of monocarboxylic acid employed are equal to the average functionality of the amine-terminated polyamide from the reaction of the polyamine and the polycarboxylic acid. At least 2.0 moles of polyamine are employed. The moles of polyamine employed are greater than or equal to the moles of polycarboxylic acid employed. The equivalents of polyamine are greater than or equal to the equivalents of polycarboxylic acid plus 2.0. The equivalents of polyamine minus the equivalents of polycarboxylic acid equal the equivalents of monocarboxylic acid.

The polyamide rheological additives of the invention are useful in both reactive systems, i.e. systems that are reactive with or are sensitive toward water or other active hydrogen containing materials and non-reactive systems, i.e. systems that do not react with or are not sensitive toward water or other active hydrogen containing materials. The invention also provides reactive composites comprising a reactive system and the polyamide rheological additives of the invention. The invention further provides non-reactive composites comprising a non-reactive system and the polyamide rheological additives of the invention.

The polyamide rheological additives of the invention provide sag or slump control when incorporated into sealant, adhesive, caulk and coating formulations and provide shear-thinning and viscosity recovery properties without impairing the properties of the end product such as package stability and cure rate.

The polyamide rheological additives of the invention provide immediate recovery of high viscosity after cessation of shear to the end use product, i.e., in less than ten seconds after application of the end use system containing the rheological additive to an end use substrate or assembly, the end use system returns to a non-flowable consistency. This property can be assessed by testing the end use system according to ASTM D2202 or ASTM C639. If during evaluation by either of these two tests the product exhibits no pronounced sagging or slumping, the recovery is considered immediate.

The polyamide rheological additives of the invention may be prepared as free-flowing powder or in combination with a solvent or plasticizer as a paste. Further, the polyamide rheological additives are effective at low use levels of from about 0.5 weight percent to about 5 weight percent loading (the weight percent being based on the total weight of the end use system), depending upon the type of system employed.

DESCRIPTION OF THE PREFERRED EMBODIMENTS

Reference will now be made in detail to the present preferred embodiments of the invention.

Exemplary suitable polycarboxylic acids for use in the invention include dimerized and trimerized fatty acids. As used herein the term "dimerized fatty acids" includes any acid obtained by dimerizing saturated, ethylenically unsaturated or acetylenically unsaturated naturally occurring or synthetic monobasic aliphatic carboxylic acids containing from 8 to 24 carbon atoms, 18 carbon atoms being quite common. Such dimerized fatty acids consist essentially of a mixture of about 36 carbon atom dicarboxylic acids and usually also contain several isomeric dimers together with a small amount of trimer and higher polymers, and are fully described in U.S. Pat. No. 4,018,733 and Empol Dimer and Polybasic Acids, A-2026, Emery Chemicals, Cincinnati, Ohio, the pertinent disclosures of which are incorporated by reference.

As used herein, the term "trimerized fatty acid" includes any acid obtained by trimerizing saturated, ethylenically unsaturated or acetylenically unsaturated naturally occurring or synthetic monobasic aliphatic carboxylic acids containing from 8 to 24 carbon atoms. Such trimerized fatty acids consist essentially of a mixture of about 54 carbon atom tricarboxylic acids and usually also contain several isomeric trimers together with a small amount of dimers, tetramers and higher polymers.

Additional exemplary suitable polycarboxylic acids include oxalic acid, glutaric acid, malonic acid, adipic acid, succinic acid, suberic acid, sebacic acid, azelaic acid, dodecanedioic acid, pimelic acid, terephthalic acid, isophthalic acid, phthalic acid, naphthalene dicarboxylic acids and 1,4- or 1,3-cyclohexane dicarboxylic acids.

In general, any polycarboxylic acid in which the carboxylic acid groups are separated by a bivalent hydrocarbon group which may be saturated or unsaturated, aliphatic, aromatic or cycloaliphatic or which may have two or more aliphatic, aromatic or cycloaliphatic moieties, can be used to form the polyamides employed in the invention. Also, any polycarboxylic acid in which the average functionality (number of functional groups per molecule) is greater than two may be used. Exemplary suitable polycarboxylic acids include 1,3,5-pentanetricarboxylic acid, 1,2,3-propanetricarboxylic acid, 1,2,3,4-butanetetracarboxylic acid and trimellitic acid. Corresponding acid anhydrides such as trimellitic anhydride, esters, and acid halides of the foregoing acids are also suitable for use in the present invention.

Exemplary suitable polyamine compounds for use in the invention include ethylene diamine, 1,2-diaminopropane, 1,3-diaminopropane, 1,4-diaminobutane, p-xylene diamine, 1,6-methylene diamine, 2-methylpentamethylene diamine, 4,4'-methylenebis(cyclohexylamine), 2,2-di-(4-cyclohexylamine)propane, polyglycol diamines, isophorone diamine, m-xylene diamine, p-phenylene diamine, 1,2-diaminocyclohexane, 1,4-diaminocyclohexane, cyclohexanebis(methylamine), bis-1,4-(2'-aminoethyl)benzene, 9-aminomethylstearylamine, 10-aminoethylstearylamine, 1,3-di-4-piperidyl propane, 1,10-diaminodecane, 1,12-diaminododecane, 1,18-diaminooctadecane, piperazine, N-aminoethylpiperazine, bis-(3-aminopropyl)piperazine, polyethylene polyamines such diethylene triamine and triethylene tetramine, diethyltoluene diamine, methylene dianiline and bis(aminoethyl)diphenyl oxide. Polymeric fat polyamines and ether polyamines may also be used. These polyamines are described in U.S. Pat. No. 4,018,733, U.S. Pat. No. 3,010,782, and The Jeffamine Polyoxyalkyleneamines, NPD-024 102-0745, Texaco Chemical Company, Bellaire Texas, the pertinent disclosures of which are incorporated herein by reference.

Exemplary suitable monocarboxylic acids for use in the invention include fatty acids. The term "fatty acids" as used herein includes saturated, ethylenically unsaturated and acetylenically unsaturated naturally occurring and synthetic monobasic aliphatic acids containing from 8 to 24 carbon atoms. Exemplary suitable saturated fatty acids include branched and straight chain acids such as caprylic acid, pelargonic acid, capric acid, lauric acid, myristic acid, palmitic acid, isopalmitic acid, stearic acid, isostearic acid, arachidic acid, behenic acid and lignoceric acid. Exemplary suitable ethylenically unsaturated acids include the branched or straight chain, poly- and mono-ethylenically unsaturated acids such as 3-octenoic acid, 11-dodecenoic acid, linderic acid, lauroleic acid, myristoleic acid, tsuzuic acid, palmitoleic acid, petroselinic acid, oleic acid, elaidic acid, vaccenic acid, gadoleic acid, cetoleic acid, nervonic acid, linoleic acid, linolenic acid, eleostearic acid, hiragonic acid, moroctic acid, timnodimic acid, eicosatetraenoic acid, nisinic acid, scoliodonic acid and chaulmoogric acid. Acetylenically unsaturated fatty acids, both straight and branched chain, both mono-unsaturated and polyunsaturated are useful herein. Exemplary suitable fatty acids include 10-undecynoic acid, tariric acid, stearolic acid, behenolic acid and isamic acid. Also, monocarboxylic acids having from two to seven carbon atoms may be used, such as acetic acid, propionic acid, butyric acid, valeric acid and caproic acid.

Exemplary suitable monoamines for use in the invention include methylamine, dimethylamine, ethylamine, diethylamine, n-propylamine, di-n-propylamine, isopropylamine, n-butylamine isobutylamine, sec-butylamine, tert-butylamine, di-n-butylamine, monoamylamine, diamylamine, ethylbutylamine, n-hexylamine, di-n-hexylamine, cyclohexylamine, benzylamine, alpha-phenylethylamine, beta-phenylethylamine, aniline, methylaniline, diphenylamine, o-toluidine, m-toluidine, p-toluidine, o-anisidine, m-anisidine, p-anisidine, dodecylamine, cocoamine, hexadecylamine, octadecylamine, oleylamine, dicocoamine, and di(hydrogenated-tallow)amine; amides such as cocoamide, octadecanamide, oleamide, o-toluene sulfonamide and p-toluene sulfonamide; and polyetheramines such as polyoxyethylene amine(s) and polyoxypropylene amines(s).

Exemplary suitable catalysts for use in the invention include acid compounds such as phosphoric acid, oxides or carbonates of an alkaline nature such as magnesium oxide or calcium oxide and halogen salts of polyvalent metals and acids. The catalyst is preferably present in an amount of from about 0% to about 3% by weight of the reactants, more preferably in an amount of from about 0.005% to about 0.500% by weight, most preferably in an amount of about 0.01% by weight of the reactants.

The ratio of equivalents of amine to acid groups for the polyamide rheological additive synthesis is preferably from about 0.8:1.0 to about 1.2 1.0 equivalents of amine to acid (NH/COOH), more preferably from about 0.95:1.00 to about 1.05:1.00 equivalents NH/COOH, most preferably about 1.0:1.0 equivalents NH/COOH.

As used herein "amine" or "NH" means any primary or secondary amine group. As used herein, "acid" or "COOH" represents any carboxylic acid, ester, acid halide or anhydride group.

In addition to the polyamide containing products formed in reactions (1)–(4) above, by-products may be formed. Except for minute quantities, the byproducts are removed during the synthesis. The byproducts formed are as follows:

carboxylic acid + amine →water
ester + amine→alcohol
acid halide + amine→hydrogen halide
anhydride + 2 amines→water Synthesis is performed in typical glass resin reaction equipment. All processing is performed under a dry nitrogen blanket or a sparge or under vacuum to prevent oxidative degradation from taking place. Vacuum processing is implemented particularly during the final stages of the reaction to remove minor amounts of water, air, other byproducts, or volatile unreacted starting materials such as amines. Vacuum processing is preferred, although not absolutely necessary.

The reactants are blended and heated gradually to 220°–240° C. During temperature elevation one or more condensers and a receiving vessel may be employed to collect the water or other byproducts of reaction as well as any volatilized starting materials. Once the reaction mass has achieved a steady state, i.e. when color, appearance, and viscosity cease to change and the acid and amine values have reached a stable minimum (preferably less than 1 mg KOH/g) each, full vacuum is applied (greater than 29 in. Hg) for a period of one or two hours. The product is then packaged and cooled. The solid product is then milled to a free-flowing powder. It is then stored until its incorporation in a sealant, adhesive or coating formulation.

Alternative method of preparation involve synthesizing the polyamide as described above and then diluting it in an appropriate plasticizer or solvent at either of two stages. The first stage dilution is described as follows. After the application of vacuum, the molten product is allowed to cool to a minimum temperature at which it is still liquid. Then the diluent is introduced while mixing. Once homogeneous, the diluted product can be degassed and discharged. The final cooled product may be a liquid, a paste or a solid.

The second stage dilution involves taking the 100% synthesized product through the milling and sieving process and then dispersing the powdered product in the diluent of choice using one of several possible methods such as a high speed dispersator or a planetary mixer. By this method, the final product may be a liquid or a paste.

The invention will be further clarified by the following examples, which are intended to be purely exemplary of the invention. All synthesis, milling, compounding and packaging operations described in the following examples are performed under a constant dry nitrogen purge unless otherwise noted.

EXAMPLE 1

Preparation of Powdered Polyamide Rheological Additive

Into a one liter resin reaction flask, 368.7 g of Empol 1010 (dimerized fatty acids, Henkel Corp., Emery Group, Cincinnati, Ohio), 8.0 g of a mixture of 1% by weight ortho-phosphoric acid and 99% by weight of Empol 1010, and 15.0 g of Sebacic Acid, CP grade (Union Camp Corp., Wayne, NJ) were charged and mixed (using an electric mixer and a dual impeller shaft) with mild heating (using a heating mantle). Once uniform, 408.2 g of Armeen 18D (octadecylamine, Akzo Chemicals, Inc., Armak Chemicals, Chicago, Illinois) were added gradually and mixed in over a 15 minute period. The reaction mixture was mixed and heated until homogeneous with all components molten. The temperature was elevated gradually to 231° C. over a period of four hours from the time when the Armeen 18D charge was completed. During this temperature elevation, vigorous bubbling was observed due to the conversion to amide and evolution of condensed water (i.e. water formed as a by product of the reaction). The temperature was maintained above 220° C. for a period of two hours, the final hour of which a vacuum of greater than 29 in. Hg was applied. The molten liquid product was then discharged into release paper lined boxes and allowed to cool overnight in a desiccator, a hard brittled solid resulted. The solid product was then broken into small fragments and milled to a powder using a Brinkmann centrifugal mill with liquid nitrogen prechilling of the fragments. The −60 mesh fraction was sieved with a 60 mesh (250%) screen (U.S. Standard Sieve Series, No. 60 (250 micron opening), Tyler equivalent =60 mesh) to remove the coarser fraction.

The powder was transferred to air-tight half-pint polypropylene jars for storage and later use. The final product was an off-white free-flowing powder.

| Test Results: | |
|---|---|
| Acid Value (mg KOH/g) | 0.6 |
| Amine Value (mg KOH/g) | 1.3 |
| Shore D Hardness | 38 |
| Ring and Ball Softening Point (°C.) | 98 |
| Brookfield Thermosel Viscosity (cP) | 55 |
| (Model RV, Spindle # SC4-27/100 rpm/120° C.) | |

EXAMPLE 2

Preparation of Paste Form

Using a Premier Dispersator with a 1 5/8 in. sawtoothed blade and a derimmed one pint can, 100.0 g PX-316 (mixed n-alkylphthalate, Aristech Chemical Corp., Pittsburgh, PA) were charged and mixed at 1000 rpm. A 100.0 g portion of the powdered polyamide from Example 1 was gradually charged over a period of six minutes. When approximately half of the powdered additive was charged, the mixer speed was increased to 2000 rpm. Once all of the powdered additive was charged, the mixer speed was increased to 5000 rpm and mixed for 14 minutes at which time a temperature of 47° C. was reached from the heat of mixing. The warm dispersion was placed in a vacuum desiccator and full vacuum (greater than 29 in. Hg) was applied for 12 minutes, and then transferred to an air-tight half-pint polypropylene jar for storage and later use. The final product was an easily workable paste of off-white to yellow color which exhibited shear-thinning and rapid recovery of viscosity.

| Test Results: | |
|---|---|
| Cone Penetration at 21° C. (mm) = | 18.5 |
| (ASTM D217, Cone Penetration Test (non-worked material, standard cone) | |

EXAMPLE 3

Preparation of Plasticized Polyurethane Sealant Prepolymer

Into a four liter resin reaction flask, 1228.8 g of Voranol 220-056 (polyoxyalkylene diol, Dow Chemical Co., Midland, Michigan) and 673.5 g of Voranol 232-034 (polyoxyalkylene triol, Dow Chemical Co., Midland, Michigan) were charged. The polyols were mixed (using an electric mixer and a three impeller shaft) and heated (using a heating mantle) to 60° C. Then 347.4 g of molten (50° C.) Isonate 2125M (4,4'-diphenylmethane diisocyanate, Dow Chemical Co., Midland, Michigan) were added and the contents of the reactor were mixed without heating for six minutes, after which the temperature was 59° C. Next, 11 drops (0.31 g) of Dabco T-9 (stannous type organometallic catalyst, Air Products and Chemicals, Inc., Allentown, Pa) were added. Two minutes later an exotherm to 90° C. was observed. After three additional minutes (at T=86° C.), 750.0 g of PX-316 (mixed n-alkylphthalate, Aristech) were added gradually over a four minute period, after which the temperature had dropped to 69° C. A vacuum was gradually applied over a 23 minute period. Full vacuum (greater than 29 in. Hg) was then maintained for 10 minutes. The resulting plasticized urethane prepolymer was then discharged into airtight high density polyethylene jars of 32 fluid ounce capacity for storage and later use.

| Test Results: | |
|---|---|
| % NCO = | 1.27 |
| Brookfield Viscosity (cP) = | 33,000 |
| (Model RV, Spindle # 6/20 rpm/23° C.) | |

EXAMPLE 4

Preparation of One-Component Moisture-Cured Polyurethane Sealant Formulation Into a two gallon Ross double planetary mixer, 393.8 g of plasticized prepolymer from Example 3 were charged, then mixed at moderate speed for 10 minutes under full vacuum (greater than 29 in. Hg). Then 930.0 g of BLR/3 (hydrophobically surface-treated calcium carbonate, Omya, Inc., Proctor, Vermont) were added and mixed in at low speed for a sufficient time for the mixture to appear homogeneous. Then a full vacuum was applied and the mixture was blended at high speed for 17 minutes. The material was scraped from the mixing blades and container walls with a steel spatula. Then 131.7 g of plasticized prepolymer from Example 3 were added and mixed in at high speed for 10 minutes under full vacuum. Again the mixing blades and container walls were scraped. Then 45.0 g of anhydrous m-Xylene were charged and mixed in at moderate speed for 12 minutes under full vacuum. The finished sealant product was then packaged into polyethylene cartridges of six fluid ounce capacity which were then placed into polyethylene lined luminum foil pouches with desiccant. The pouches were then heat-sealed for storage and subsequent evaluation. The tests and results are set forth in Table I.

EXAMPLE 5

Preparation of One-Component Moisture-Cured Polyurethane Sealant Formulation A Using the same equipment and procedure as in Example 4, a sealant was prepared. A heated water jacket was employed to maintain a batch temperature of 60° C. during and following the incorporation of the modifying additive described below. The same components and quantities as described in Example 4 were used with one exception. Instead of incorporating 930.0 g BLR/3, the following two items were incorporated at the same stage of manufacture: 907.5 g of BLR/3 and 22.5 g of the powdered rheological additive prepared in Example 1. The finished sealant product was packaged as in Example 4. The tests and results are set forth in Table I.

EXAMPLE 6

Preparation of One-Component Moisture-Cured Polyurethane Sealant Formulation B Using the same equipment and procedure as in Example 5, a sealant was prepared. The same components and quantities were used but with the following exception. Instead of incorporating 907.5 g of BLR/3 and 22.5 g of the additive from Example 5, the following two items were incorporated at the same stage of manufacture: 870.0 g of BLR/3 and 60.0 g of the paste form of rheological additive prepared in Example 2. The finished sealant product was packaged as in Example 5. The tests and results are set forth in Table I. The incorporation of the powdered polyamide or the paste form shown in Table I both provided for excellent control of sag and slump to an otherwise fluid, self-leveling sealant composition. No impairment of extrudability, curability or package stability was observed.

TABLE I

| | Sealant Test Results | | |
|---|---|---|---|
| Example | 4 | 5 | 6 |
| Rheological Additive | None | Example 1 (powder) | Example 2 (paste) |
| Weight Percent Rheological Additive | — | 1.5 | 2.0 |
| Moisture Curability of Thin (approx. 50 mil) Film | Cured Through Overnight Non-Tacky | Cured Through Overnight Non-Tacky | Cured Through Overnight Non-Tacky |
| Package Stability | No Appreciable Change in Viscosity or Appearance Upon Ambient Aging For 7 Days | No Appreciable Change in Viscosity or Appearance Upon Ambient Aging For 7 Days | No Appreciable Change in Viscosity or Appearance Upon Ambient Aging For 7 Days |
| R.T. Flow Rate SAE Vis-2 Castor-Severs Flowmeter 20 grams, 0.104 in. Orifice | | | |
| 40 psi (sec.) | 44 | 99 | 99 |
| 80 psi (sec.) | 20 | 40 | 39 |
| ASTM D2202, Modified Boeing Slump Test 60 Min. at R.T. (In.) | Greater than 4.00 (after 30 sec.) | 0.02 | 0.02 |
| ASTM C639, Modified Vertical Channel Sag Test 60 Min. at R.T. (In.) | Too Fluid To Test | 0.15 | 0.10 |
| Bohlin Rheometer System Measuring System: CP 5/30 Torque Element: 289.145 g cm | | | |
| Shear Rate ($s^{-1}$) | Viscosity* | Viscosity* | Viscosity* |
| 0.1172 | 486.8 | 1471 | 1123 |
| 14.75 | 165.4 | 209.3 | 170.4 |
| T.I. = $\frac{(Pa \cdot s) \text{ at } 1172 \, s^{-1}}{(Pa \cdot s) \text{ at } 14.75 \, s^{-1}}$ | 2.94 | 7.03 | 6.59 |

*Pa · s

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A rheological additive providing viscosity control in resin or organic solvent systems comprising a monoamine capped non-reactive polyamide.

2. The rheological additive of claim 1 wherein the polyamide is prepared by reacting at least one polycarboxylic acid of the formula (I)

$$(A)[COOH]_x \qquad (I)$$

wherein $x \geq 2$ and A is selected from the group consisting of aliphatic, aromatic, cycloaliphatic, and arylaliphatic groups, with at least one monoamine.

3. The rheological additive of claim 2 wherein the polycarboxylic acid is selected from the group consisting of dimerized fatty acids, trimerized fatty acids, dicarboxylic acids containing from 6 to 22 carbon atoms, and tricarboxylic acids containing from 6 to 22 carbon atoms.

4. The rheological additive of claim 3 wherein the polycarboxylic acid is selected from the group consisting of dimer acids, trimer acids, sebacic acid, azelaic acid and dodecanedioic acid.

5. The rheological additive of claim 2 wherein the monoamine is selected from the group consisting of saturated, ethylenically unsaturated and acetylenically unsaturated naturally occurring and synthetic primary and secondary monoamines containing from 8 to 24 carbon atoms.

6. The rheological additive of claim 5 wherein the monoamine is selected from the group consisting of octadecylamine, dodecylamine and oleylamine.

7. A sealant composition containing a rheological additive providing viscosity control wherein said rheological additive comprises the polyamide of claim 1.

8. A caulk composition containing a rheological additive providing viscosity control wherein said rheological additive comprises the polyamide of claim 1.

9. An adhesive composition containing a rheological additive providing viscosity control wherein said rheological additive comprises the polyamide of claim 1.

10. A coating composition containing a rheological additive providing viscosity control wherein said rheological additive comprises the polyamide of claim 1.

11. A paste composition containing a rheological additive providing viscosity control wherein said rheological additive comprises the polyamide of claim 1.

* * * * *